United States Patent [19]

Ishikawa et al.

[11] Patent Number: 4,594,347
[45] Date of Patent: Jun. 10, 1986

[54] PYRROLO [3,2,1-IJ]-QUINOLINE CARBOXYLIC ACID COMPOUND

[75] Inventors: Hiroshi Ishikawa, Otsu; Tetsuyuki Uno, Tokushima; Hisashi Miyamoto, Tokushima; Kazuyuki Nakagawa, Tokushima, all of Japan

[73] Assignee: Otsuka Pharmaceutical Co. Limited, Tokyo, Japan

[21] Appl. No.: 573,409

[22] Filed: Jan. 24, 1984

[30] Foreign Application Priority Data

Jan. 26, 1983 [JP]  Japan ............................ 58-11837

[51] Int. Cl.$^4$ ................. C07D 403/04; C07D 401/04; A61K 31/495
[52] U.S. Cl. ................... 514/252; 544/361; 544/372
[58] Field of Search ............... 544/361, 372; 424/250; 514/252

[56] References Cited

U.S. PATENT DOCUMENTS 3,917,609 11/1975 Gerster ..................... 544/361
4,399,134 11/1983 Ishikawa et al. ............ 544/361
4,416,884 11/1983 Ishikawa et al. ............ 544/361

FOREIGN PATENT DOCUMENTS 2264163 12/1972 Fed. Rep. of Germany .
2914258  4/1979 Fed. Rep. of Germany .
3037103 10/1980 Fed. Rep. of Germany .
3144455 11/1981 Fed. Rep. of Germany .
  40616  3/1980 Japan ..................... 544/361
2091726  8/1982 United Kingdom ......... 544/361
2020279  8/1982 United Kingdom ......... 544/361

Primary Examiner—George F. Lesmes
Assistant Examiner—S. A. Gibson
Attorney, Agent, or Firm—Wegner & Bretschneider

[57] ABSTRACT

Benzo-heterocyclic compounds of the formula:

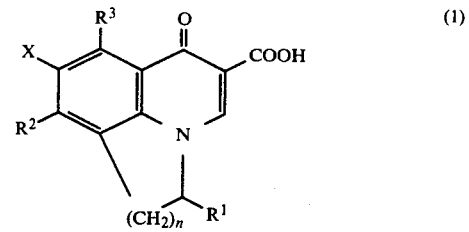

wherein $R^1$ is a lower alkyl group; $R^2$ is a halogen atom or a group of the formula

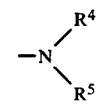

(wherein $R^4$ and $R^5$ combine together with the nitrogen atom to which they bind to form a 5- or 6-membered saturated heterocyclic group which may optionally contain an oxygen atom or nitrogen atom within the ring as an additional hetero atom and may also optionally have a substituent selected from a lower alkyl or hydroxy group on the hetero ring); $R^3$ is an amino or nitro group; X is a halogen atom; and n is an integer of 1 or 2, and a salt thereof, which have excellent antimicrobial activities and are useful as an antimicrobial agent, or as an intermediate for the preparation of an active compound.

5 Claims, No Drawings

PYRROLO [3,2,1-IJ]-QUINOLINE CARBOXYLIC ACID COMPOUND

The present invention relates to novel benzoheterocyclic compounds or their salts. More particularly, it relates to benzoheterocyclic compounds of the formula:

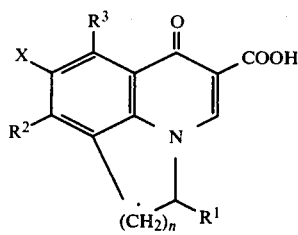

wherein $R^1$ is a lower alkyl group; $R^2$ is a halogen atom or a group of the formula:

(wherein $R^4$ and $R^5$ combine together with the nitrogen atom to which they bind to form a 5- or 6-membered saturated heterocyclic group which may optionally contain an oxygen atom or nitrogen atom within the ring as an additional hetero atom and may also optionally have a substituent selected from a lower alkyl or hydroxy group on the hetero ring); $R^3$ is an amino or nitro group; X is a halogen atom; and n is an integer of 1 or 2, and a salt thereof.

The compounds (1) of the present invention have excellent antimicrobial activities against various gram-positive bacteria and gram-negative bacteria with low toxicity and less side effect, and hence, are useful as an antimicrobial agent for the treatment of various diseases induced by various bacteria in human beings and other animals and various fishes, and further are useful as a sterilizer or disinfectant of various medical instruments or the like. The compounds of the present invention show particularly excellent antimicrobial activities against Pseudomonas aeruginosa, microorganisms unfermentable with glucose, gram-negative bacteria, clinically isolated strains, or the like. Moreover, the compounds of the present invention are easily absorbed into a body and can exhibit their excellent antimicrobial activities in the body with a high excretion rate into urine, and hence, are useful for the treatment of urinary infectious diseases, and are also useful for the treatment of intestinal infectious diseases because they are also easily excreted via bile. Besides, the compounds of the formula (1) wherein $R^2$ is a halogen atom are also useful as an intermediate for the preparation of a compound having excellent antimicrobial activities.

In the present specification, the groups for $R^1$, $R^2$, $R^3$, $R^4$, $R^5$ and X in the formula (1) includes the following groups.

The group "lower alkyl" denotes a straight or branched alkyl having 1 to 6 carbon atoms, such as methyl, ethyl, propyl, isopropyl, butyl, tert-butyl, pentyl, hexyl, or the like. "Halogen atom" includes fluorine, chlorine, bromine and iodine.

The "5- or 6-membered saturated heterocyclic group which may optionally have a substituent selected from a lower alkyl or hydroxy group" denotes a 5- or 6-membered cyclic amine having a substituent selected from a straight or branched alkyl having 1 to 6 carbon atoms or a hydroxy group, and includes, for example, 1-piperazinyl, 4-methyl-1-piperazinyl, 3-ethyl-1-piperazinyl, 2-propyl-1-piperazinyl, 4-butyl-1-piperazinyl, 4-pentyl-1-piperazinyl, 3-hexyl-1-piperazinyl, 4-hydroxy-1-piperazinyl, 3-hydroxy-1-piperazinyl, 2-hydroxy-1-piperazinyl, 1-piperidyl, 4-methyl-1-piperidyl, 3-ethyl-1-piperidyl, 2-propyl-1-piperidyl, 4-butyl-1-piperidyl, 4-pentyl-1-piperidyl, 3-hexyl-1-piperidyl, 4-hydroxy-1-piperidyl, 3-hydroxy-1-piperidyl, 2-hydroxy-1-piperidyl, morpholino, 3-methylmorpholino, 2-ethylmorpholino, 3-propylmorpholino, 3-butylmorpholino, 3-hexylmorpholino, 3-hydroxymorpholino, 2-hydroxymorpholino, 1-pyrrolidinyl, 3-methyl-1-pyrrolidinyl, 2-ethyl-1-pyrrolidinyl, 3-propyl-1-pyrrolidinyl, 2-butyl-1-pyrrolidinyl, 3-pentyl-1-pyrrolidinyl, 3-hexyl-1-pyrrolidinyl, 3-hydroxy-1-pyrrolidinyl, 2-hydroxy-1-pyrrolidinyl, or the like.

Among the compounds of the formula (1), preferred compounds are compounds of the formula (1) wherein $R^1$ is methyl or ethyl group, more preferably methyl group; X is chlorine or fluorine, more preferably fluorine; $R^2$ is a group of the formula:

($R^4$ and $R^5$ are as defined above), more preferably $R^2$ is a substituted or unsubstituted 1-piperazinyl group, particularly a 4-lower alkyl substituted 1-piperazinyl group; and $R^3$ is an amino group. Particularly preferred compounds are compounds of the formula (1) wherein $R^1$ is the methyl group, $R^2$ is a 4-lower alkyl substituted 1-piperazinyl group, $R^3$ is amino group, X is fluorine, and n is an integer of 1 or 2.

The compounds (1) of the present invention can be prepared by various processes. A suitable example of the processes is illustrated by the following Reaction Scheme-I.

Reaction Scheme-I

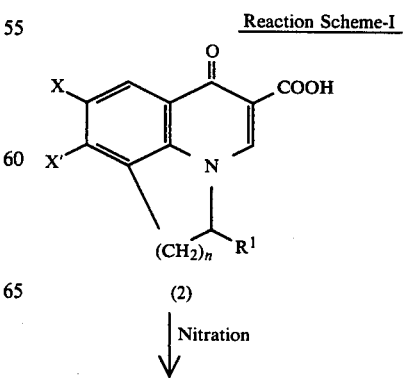

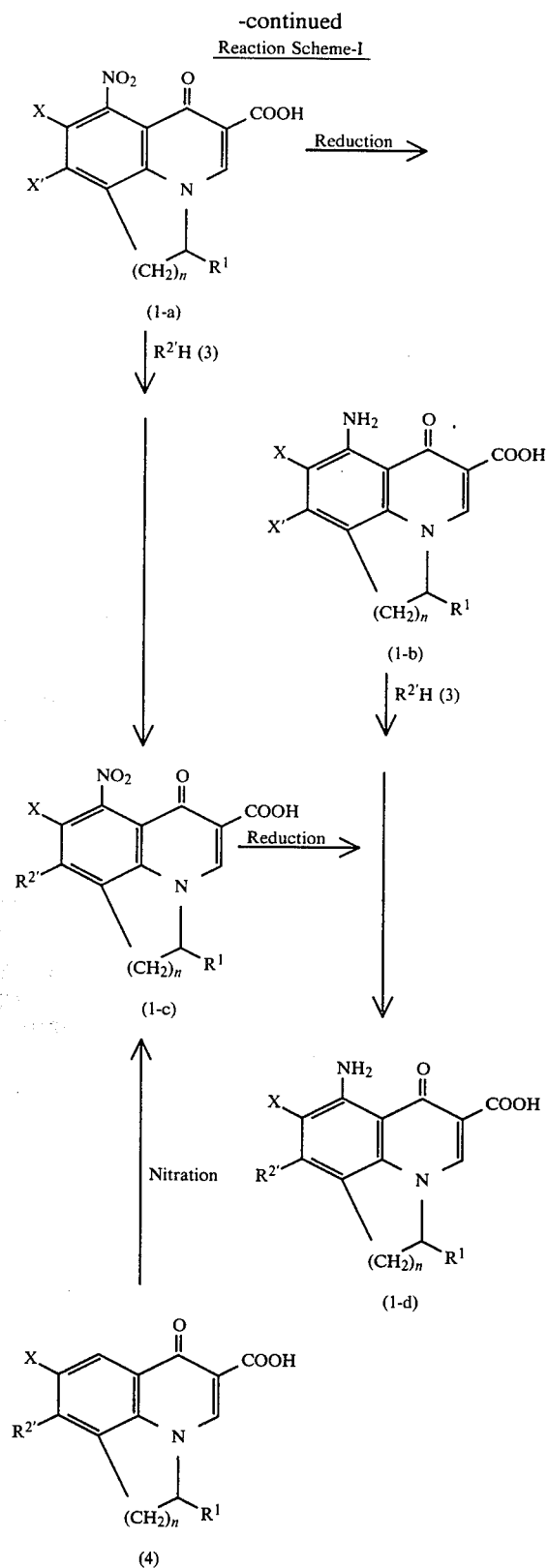

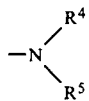

(wherein R[4] and R[5] are as defined above).

In the above Reaction Scheme-I, the nitration of the compound (2) or (4) is carried out under the conditions which are usually employed in the nitration of aromatic compounds, for example, by treating the compound (2) or (4) with a nitrating agent in an inert solvent or in the absence of a solvent. The inert solvent includes acetic acid, acetic anhydride, conc. sulfuric acid, or the like. The nitrating agent includes fuming nitric acid, conc. nitric acid, mixed acid (i.e. a mixture of nitric acid with other acid selected from sulfuric acid, fuming sulfuric acid, phosphoric acid or acetic anhydride), a combination of an alkali metal nitrate (e.g. potassium nitrate, sodium nitrate) and sulfuric acid. The nitrating agent is used in an equimolar amount or more, usually in an excess amount, to the amount of the starting compound (2) or (4). The reaction is preferably carried out at a temperature of 0° to 100° C. for 1 to 4 hours.

The starting compounds (2) and (4) are known compounds. In the compounds (2), the halogen atom for the group X' includes fluorine, chlorine, bromine and iodine. The "lower alkane-sulfonyloxy group" includes methanesulfonyloxy, ethane-sulfonyloxy, propanesulfonyloxy, isopropanesulfonyloxy, butanesulfonyloxy, tert-butanesulfonyloxy, pentanesulfonyloxy, hexanesulfonyloxy, or the like. The "arylsulfonyloxy group" includes substituted or unsubstituted arylsulfonyloxy groups, such as phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, α-naphthylsulfonyloxy or the like. The "arylalkanesulfonyloxy group" includes substituted or unsubstituted arylalkanesulfonyloxy groups, such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethylsulfonyloxy, or the like.

The reduction of the compound (1-a) is carried out, for example, by (i) catalytically reducing it with a catalytic reducing agent in a solvent, or (ii) reducing it with a reducing agent, such as a combination of a metal or metal salt and an acid, or a combination of a metal or metal salt and an alkali metal hydroxide, sulfide or ammonium salt in an inert solvent. In the catalytic reduction (i), the solvent includes water, acetic acid, an alcohol (e.g. methanol, ethanol, isopropanol), a hydrocarbon (e.g. hexane, cyclohexane), an ether (e.g. diethyleneglycol dimethylether, dioxane, tetrahydrofuran, diethyl ether), an ester (e.g. ethyl acetate, methyl acetate), an aprotic polar solvent (e.g. N,N-dimethylformamide). The catalytic reducing agent includes, for example, palladium, palladium black, palladium carbon, platinum, platinum oxide, copper chromite, of Raney nickel. The catalyst is used in an amount of 0.02 to 1.00 part by weight to 1 part by weight of the compound (1-a). The reaction is usually carried out at a temperature of −20° to 150° C., preferably 0° C. to room temperature, under a hydrogen pressure of 1 to 10 atm for about 0.5 to 10 hours. In the method (ii), there are used as the reducing agent a combination of a metal or metal salt selected In the above formulae, R[1], X and n are as defined above, X' is a halogen atom, a lower alkanesulfonyloxy group, an arylsulfonyloxy group or an arylalkanesulfonyloxy group, and R[2'] is a group of the formula:

from iron, zinc, tin or stannous chloride and a mineral acid selected from hydrochloric acid or sulfuric acid, and a combination of a metal or metal salt selected from iron, ferrous sulfate, zinc or tin and an alkali metal hydroxide (e.g. sodium hydroxide), a sulfide (e.g. ammonium sulfide), aqueous ammonia, or an ammonium salt (e.g. ammonium chloride). The inert solvent includes, for example, water, acetic acid, methanol, ethanol, dioxane, or the like. The reaction conditions may vary according to the kinds of reducing agents. In one embodiment using a reducing agent of a combination of stannous chloride and hydrochloric acid, the reaction is preferably carried out at a temperature of 0° C. to 100° C. for about 0.5 to 10 hours. The reducing agent is usually used in an amount of at least one mole, preferably 1 to 5 moles, to 1 mole of the compound (1-a).

In the reaction of the compounds (1-a) or the compound (1-b) with the compound (3), the amounts of both compounds are not specified, but the former compound (1-a) or (1-b) is usually used in an amount of at least one mole, preferably 1 to 5 moles, to 1 mole of the latter compound (3). The reaction is usually carried out in an inert solvent. Suitable examples of the solvent are water, alcohols (e.g. methanol, ethanol, isopropanol, butanol, amyl alcohol, isoamyl alcohol), aromatic hydrocarbons (e.g. benzene, toluene, xylene), ethers (e.g. tetrahydrofuran, dioxane, diglyme), dimethylsulfoxide, dimethylformamide, hexamethylphosphoric acid triamide, N-methylpyrrolidone, or the like. The reaction may optionally be carried out in the presence of a base. Suitable examples of the base are inorganic carbonates (e.g. sodium carbonate, potassium carbonate, sodium hydrogen carbonate, potassium hydrogen carbonate), tertiary amines (e.g. pyridine, quinoline, triethylamine), or the like. The reaction is usually carried out under a pressure of 1 to 20 atm., preferably 1 to 10 atm., at a temperature of 100° to 250° C., preferably 100° to 200° C., for about 1 to 20 hours. In such a manner, there are obtained the compounds (1-c) and (1-d) of the present invention.

The compound (1-d) is also prepared by reducing the compound (1-c) under the same conditions as those in the reduction of the compound (1-a) as mentioned above.

The compounds of the present invention can also be prepared by the process as shown in the following Reaction Scheme-II.

Reaction Scheme-II

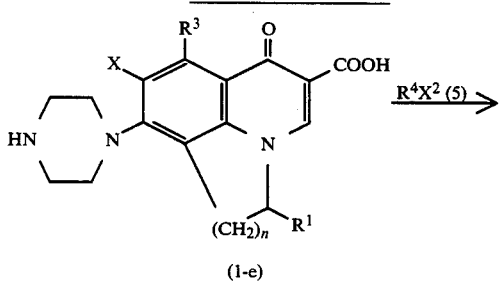

(1-e)

-continued
Reaction Scheme-II

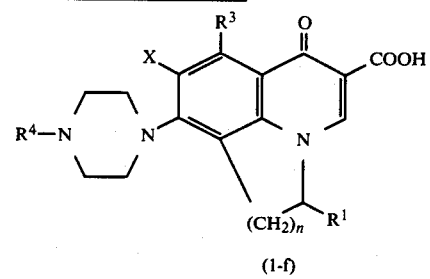

(1-f)

wherein $R^1$, $R^3$, X and n are as defined above, $R^4$ is a lower alkyl group, and $X^2$ is a halogen atom.

The above reaction can be carried out by a conventional dehydrohalogenation reaction. More particularly, the above reaction can be carried out in a solvent such as water, lower alcohols (e.g. methanol, ethanol, isopropanol), ketones (e.g. acetone, methyl ethyl ketone), ethers (e.g. diethyl ether, dioxane), and aromatic hydrocarbons (e.g. benzene, toluene, xylene) in the presence of a suitable dehydrohalogenating agent such as sodium hydroxide, potassium hydroxide, potassium carbonate, sodium carbonate, sodium metal, potassium metal, pyridine, piperidine and the like. The compound (5) is used in an amount of 1 mole to excess amount, preferably 1 to 3 moles, per 1 mole of the compound (1-e). The reaction can proceed at a temperature of from room temperature to 150° C., preferably 50° to 120° C., for about 1 to 12 hours.

The compounds of the formula (1) can easily be converted into their pharmaceutically acceptable salts by treating them with a pharmaceutically acceptable acid or basic compound. Suitable examples of the acid are inorganic acids such as hydrochloric acid, sulfuric acid, phosphoric acid, or hydrobromic acid; organic acids such as oxalic acid, maleic acid, fumaric acid, malic acid, tartaric acid, citric acid, or benzoic acid. Suitable examples of the basic compound are sodium hydroxide, potassium hydroxide, calcium hydroxide, sodium carbonate, potassium hydrogen carbonate, or the like.

The compounds of the present invention thus prepared can be isolated from the reaction mixture and purified by conventional methods, such as extraction with a solvent, dilution method, recrystallization, column chromatography, preparative thin layer chromatography, or the like.

The compounds (1) or their pharmaceutically acceptable salts of the present invention are useful as an antimicrobial agent and are usually used in the form of conventional pharmaceutical preparations. The pharmaceutical preparations can be prepared by using conventional diluents and carriers such as fillers, bulking agents, binding agents, wetting agents, disintegrators, surface active agents, lubricants, or the like. the preparations may be in various forms, such as tablets, pills, powders, solutions, suspentions, emulsions, granules, capsules, suppositories, injections (solution, suspension, etc.), and the like. The tablets can be prepared by using conventional carriers, such as excipients (e.g. lactose, sucrose, sodium chloride, glucose, urea, starches, calcium carbonate, kaolin, crystalline cellulose, silicic acid, etc.), binding agents (e.g. water, ethanol, propanol, simple syrup, aqueous glucose solution, aqueous solution of starches, aqueous gelatine solution, carboxymethyl cellulose, shellac, methyl cellulose, potassium phosphate, polyvinyl pyrrolidone, etc.), disintegrators (e.g. dry starches, sodium arginate, agar powder, laminaran powder, sodium hydrogen carbonate, calcium carbonate, polyoxyethylene sorbitan fatty acid esters, sodium laurylsulfate, monoglyceryl stearate, starches, lactose, etc.), disintegration inhibitors (e.g. sucrose, stearin, cacao butter, hydrogenated oils, etc.), absorption accelerators (e.g. quaternary ammonium salt, sodium laurylsulfate, etc.), humectants (e.g. glycerin, starches, etc.), adsorbents (e.g. starches, lactose, kaolin, bentonite, colloidal silica, etc.), lubricants (e.g. purified talc, stearic acid salts, boric acid powder, polyethylene glycol, etc.), and the like. The tablets may be in the form of sugar coating tablets, gelatin coating tablets, enteric coating tablets, film coating tablets, double or multiple layers tablets, and the like. The pills can be prepared by using conventional carriers, such as excipients (e.g. glucose, lactose, starches, cacao butter, hardened vegetable oils, kaolin, talc, etc.), binding agents (e.g. gum arabic powder, tragacanth powder, gelatin, ethanol, etc.), disintegrators (e.g. laminaran, agar, etc.), and the like. The suppositories can be prepared by using conventional carriers, such as polyethylene glycol, cacao butter, higher alcohols or their esters, gelatin, semisynthetic glycerides, or the like. When the active compounds are prepared in the form of an injection, a solution or suspension containing the active compounds is sterilized and made isotonic to blood. The injections in the form of a solution, emulsion or suspension can be prepared by using conventional diluents, such as water, ethyl alcohol, propylene glycol, ethoxylated isostearyl alcohol, polyoxy-isostearyl alcohol, polyoxyethylene sorbitan fatty esters, or the like. The injection preparation may be made isotonic by adding thereto a sufficient amount of sodium chloride, glucose, glycerin, or the like and may optionally be incorporated with conventional solubilizers, buffer solutions, pain killers, colorants, preservatives, perfumes, flavors, sweetening agents, and other medicaments. The preparations in the form of a paste, cream or gel can be prepared by using the conventional diluents which are usually used for these preparations, for example, white vaseline, paraffin, glycerin, cellulose derivatives, polyethylene glycol, silicone, bentonite, or the like.

The preparations of the present invention may contain a wide range of amount of the active compounds and contains usually about 1 to 70% by weight of the active compounds of the present invention based on the total weight of the preparations.

The administration route of the preparations of the present invention is not restricted, and a suitable administration route is determined by the forms of the preparations, age, sex and other conditions of patients to be treated, severity of disease, and the like. Tablets, pills, solutions, suspensions, emulsions, granules and capsules are usually administered in oral route. Injections are usually administered in intravenous route alone or optionally together with an appropriate adjuvant such as glucose or amino acids or may be administered alone in intramuscular, intracutaneous, subcutaneous, or intraperitoneal route.

The dose of the active compounds of the present invention may vary with the usage, age, sex and other conditions of patients to be treated, severity of disease, or the like, but is usually in the range of 0.2 to 100 mg/kg of body weight per day, which is usually divided into 3 to 4 times.

The present invention is illustrated by the following Examples, Preparations and antimicrobial tests.

EXAMPLE 1

8,9-Difluoro-2-methyl-6-oxo-1,2-dihydro-pyrrolo[3,2,1-ij]quinoline-5-carboxylic acid (11.5 g) is dissolved in conc. sulfuric acid (120 ml), and thereto is added potassium nitrate (17 g), and the mixture is reacted at an inner temperature of 70° C. for 2 hours. After the reaction, the reaction mixture is added to ice-water (1 liter), and the precipitated crystals are separated by filtration and recrystallized from dimethylformamide to give 8,9-difluoro-2-methyl-7-nitro-6-oxo-1,2-dihydro-pyrrolo[3,2,1-ij]quinoline-5-carboxylic acid (6.8 g) as white cubic crystals. m.p. 265°–268° C. (decomp.)

EXAMPLE 2

8,9-Difluoro-2-methyl-7-nitro-6-oxo-1,2-dihyro-pyrrolo[3,2,1-ij]quinoline-5-carboxylic acid (6 g) is dissolved in dimethylformamide (300 ml) and thereto is added 20% palladium-carbon catalyst (0.5 g), and the mixture is subjected to a catalytic reduction under a pressure of 5 kg/cm$^2$. After the reaction, the cartalyst is filtered off and further dimethylformamide is distilled off, and to the residue is added ethanol. The resulting precipitated crystals are separated by filtration and recrystallized from dimethylformamide to give 8,9-difluoro-2-methyl-7-amino-6-oxo-1,2-dihydro-pyrrolo[3,2,1-ij]quinoline-5-carboxylic acid (2.7 g) as yellow cubic crystals. m.p. 270°–274° C. (decomp.)

EXAMPLE 3

8,9-Difluoro-7-amino-2-methyl-6-oxo-1,2-dihydro-pyrrolo[3,2,1-ij]quinoline-5-carboxylic acid (2 g) and N-methylpiperazine (4 ml) are suspended in N-methylpyrrolidone (20 ml), and the mixture is heated at 110°–120° C. on an oil bath for 3 hours. After the reaction, the reaction mixture is distilled under reduced pressure, and to the residue is added ethyl acetate. The resulting crystals are separated by filtration and thereto is added water (80 ml), which is regulated to pH 2 with 6N hydrochloric acid, and the mixture is heated at 50° C. and then filtered. The filtrate is concentrated to dryness, and the residue is recrystallized from ethanol-water to give yellow cubic crystals. The crystals are again suspended in water (10 ml) and is dissolved by regulating to pH 12 with a 10% aqueous sodium hydroxide solution and then is regulated to pH 8 with acetic acid. The precipitated crystals are separated by filtration, washed with water and dried to give 8-fluoro-2-methyl-9-(4-methyl-1-piperazinyl)-7-amino-6-oxo-1,2-dihydro-pyrrolo[3,2,1-ij]quinoline-5-carboxylic acid (1.4 g) as yellow cubic crystals. m.p. 240°–243° C.

EXAMPLE 4

In the same manner as described in Example 3, 8,9-difluoro-7-amino-2-methyl-6-oxo-1,2-dihydro-pyrrolo[3,2,1-ij]quinoline-5-carboxylic acid (3 g), anhydrous piperazine (4.6 g) and N-methylpyrrolidone (30 ml) are treated to give 8-fluoro-2-methyl-9-(1-piperazinyl)-7-amino-6-oxo-1,2-dihydro-pyrrolo[3,2,1-ij]quinoline-5-carboxylic acid (2.1 g), as pale yellow cubic crystals. m.p. 256°–259° C. (decomp.)

EXAMPLE 5

7-Amino-8,9-difluoro-2-methyl-6-oxo-1,2-dihydro-pyrrolo[3,2,1-ij]quinoline-5-carboxylic acid (1.0 g) and morpholine (1.5 g) are suspended in N-methylpyrrolidone (10 ml), and the mixture is heated to 110°–120° C. for 5 hours in a sealed tube. The reaction mixture is concentrated to dryness under reduced pressure, and to the residue is added ethyl acetate. The resulting crystals are separated by filtration and recrystallized from N,N-dimethylformamide to give 7-amino-8-fluoro-9-(4-morpholino)-2-methyl-6-oxo-1,2-dihydro-pyrrolo[3,2,1-ij]quinoline-5-carboxylic acid (0.6 g) as yellow cubic crystals. m.p. higher than 300° C.

Elementary analysis for $C_{17}H_{18}N_3O_4F$: Calcd. (%): C,58.78; H,5.22; N,12.10, Found (%): C,58.66; H,5.27; N,12.01.

EXAMPLE 6

7-Amino-8,9-difluoro-2-methyl-6-oxo-1,2-dihydro-pyrrolo[3,2,1-ij]quinoline-5-carboxylic acid (0.5 g) and piperidine (0.8 g) are suspended in N-methylpyrrolidone (10 ml), and the mixture is heated at 110°–120° C. for 5 hours in a sealed tube. The reaction mixture is concentrated to dryness under reduced pressure, and to the residue is added ethyl acetate. The resulting crystals are separated by filtration and recrystallized from N,N-dimethylformamide to give 7-amino-8-fluoro-2-methyl-6-oxo-9-(1-piperidyl)-1,2-dihydro-pyrrolo[3,2,1-ij]quinoline-5-carboxylic acid (0.3 g) as yellow cubic crystals. m.p. 273°–276° C. (decomp.)

EXAMPLE 7

7-Amino-8,9-difluoro-2-methyl-6-oxo-1,2-dihydro-pyrrolo[3,2,1-ij]quinoline-5-carboxylic acid (0.5 g) and 4-hydroxypiperidine (1.0 g) are suspended in N-methyl-pyrrolidone (5 ml), and the mixture is heated at 110°–120° C. for 5 hours. The reaction mixture is concentrated to dryness under reduced pressure, and to the residue is added ethanol. The resulting crystals are separated by filtration and recrystallized from N,N-dimethylformamide to give 7-amino-8-fluoro-9-(4-hydroxy-1-piperidyl)-2-methyl-6-oxo-1,2-dihydro-pyrrolo[3,2,1-ij]quinoline-5-carboxylic acid (0.2 g) as yellow cubic crystals. m.p. 287°–292° C. (decomp.)

EXAMPLE 8

7-Amino-8,9-difluoro-2-methyl-6-oxo-1,2-dihydro-pyrrolo[3,2,1-ij]quinoline-5-carboxylic acid (0.5 g) and pyrrolidine (0.7 g) are suspended in N-methylpyrrolidone (10 ml), and the mixture is heated at 110°–120° C. for 5 hours in a sealed tube. The reaction mixture is concentrated to dryness under reduced pressure, and to the residue is added ethyl acetate. The resulting crystals are separated by filtration and recrystallized from N,N-dimethylformamide to give 7-amino-8-fluoro-2-methyl-6-oxo-9-(1-pyrrolidinyl)-1,2-dihydro-pyrrolo[3,2,1-ij]quinoline-5-carboxylic acid (0.2 g) as yellow cubic crystals. m.p. 296°–299° C. (decomp.)

EXAMPLE 9

8-Bromo-9-fluoro-5-methyl-6,7-dihydro-1-oxo-1H,5H-benzo[i,j]quinolidine-2-carboxylic acid (17.1 g) is dissolved in conc. sulfuric acid (180 ml), and thereto is added potassium nitrate (25.3 g), and the mixture is stirred at 65°–70° C. for 3 hours. The reaction mixture is poured onto ice (1 kg), and the precipitated brown crystal is separated by filtration and washed with water to give 8-bromo-9-fluoro-5-methyl-10-nitro-6,7-dihydro-1-oxo-1H,5H-benzo[i,j]quinolidine-2-carboxylic acid (10.5 g) as pale yellow needles. m.p. higher than 300° C. (recrystallized from glacial acetic acid)

Elementary analysis for $C_{14}H_{10}N_2O_5FBr$: Calcd. (%): C,43.66; H,2.62; N,7.27, Found (%): C,43.59; H,2.55; N,7.34.

EXAMPLE 10

8-Bromo-9-fluoro-5-methyl-10-nitro-6,7-dihydro-1-oxo-1H,5H-benzo[i,j]quinolidine-2-carboxylic acid (4.6 g) is dissolved in glacial acetic acid (300 ml), and thereto is added a solution of stannous chloride (11.6 g) in conc. hydrochloric acid (10 ml), while stirring at 110°–120° C. The mixture is stirred at the same temperature for 1.5 hour. The reaction mixture is concentrated to dryness under reduced pressure, and the residue is washed well with water to give 10-amino-8-bromo-9-fluoro-5-methyl-6,7-dihydro-1-oxo-1H,5H-benzo[i,j]quinolidiene-2-carboxylic acid (1.32 g) as yellow needles. m.p. higher than 300° C.

Elementary analysis for $C_{14}H_{12}N_2O_3FBr$: Calcd. (%): C,47.34; H,3.41; N,7.89, Found (%): C,47.45; H,3.47; N,7.82.

EXAMPLE 11

To a mixture of 10-amino-8-bromo-9-fluoro-5-methyl-6,7-dihydro-1-oxo-1H,5H-benzo[i.j]quinolidine-2-carboxylic acid (730 mg) and N-methylpiperadine (1.14 ml) is added hexamethylphophoric triamide (10 ml), and the mixture is stirred at 150°–160° C. for 10 hours. After distilling off the solvent under reduced pressure, the residue is washed with ethyl acetate (80 ml). The resulting crystal is dissolved in 0.2N HCl (50 ml) while heating at 50° C. and then treated with activated carbon. Insoluble materials are filtered off, and the filtrate is concentrated to dryness under reduced pressure. The residue is dissolved in water (10 ml) and is regulated to pH 8–9 with an aqueous saturated sodium carbonate solution. The precipitated crystal is separated by filtration and is recrystallized from ethanol to give 10-amino-9-fluoro-5-methyl-8-(4-methyl-1-piperazinyl)-6,7-dihydro-1-oxo-1H,5H-benzo[i,j]quinolidine-2-carboxylic acid (60 mg) as yellow needles. m.p. 293°–295° C.

EXAMPLE 12

To a mixture of 9-(1-piperazinyl)-8-fluoro-7-amino-2-methyl-1,2-dihydro-6-oxo-pyrrolo[3,2,1-ij]quinoline-5-carboxylic acid (3.45 g) and dimethylformamide (20 ml) is added a dimethylformamide solution (20 ml) of trifluoromethyl iodide containing methyl iodide (7.7 g), and the mixture is reacted in a stainless steel autoclave on an oil bath at 110°–120° C. for 5 hours. After completion of reaction, dimethylformamide is distilled off under reduced pressure, and to the residue is added a 10% aqueous sodium hydroxide solution. Insoluble materials are removed by filtration. The filtrate is regulated to pH 8 with acetic acid, and the precipitated crystal is separated by filtration, washed with water, and dried to give 9-(4-methyl-1-piperazinyl)-8-fluoro-7-amino-2-methyl-1,2-dihydro-6-oxo-pyrrolo[3,2,1-ij]quinoline-5-carboxylic acid (1.82 g) as yellow cubic crystals. m.p. 240°–243° C.

TEST 1

(Antimicrobial test in vitro)

The antimicrobial activities of the following test compounds were tested by measuring the minimum inhibitory concentration (MIC) by an agar plate dilution method [cf. Chemotherapy, 22, 1126–1128 (1974)]. The test results are shown in Table 1. The test microorganisms were used in a concentration of $1 \times 10^8$ cells/ml (optical dencity (O.D.) at 660 m: 0.07–0.16) and $1 \times 10^6$ cells/ml (dilution: 100 folds).

[Test compounds]
1. Compound of Example 3
2. Compound of Example 4
3. Compound of Example 5
4. Compound of Example 6
5. Compound of Example 7
6. Compound of Example 8
7. Reference compound: 8-fluoro-2-methyl-6-oxo-9-(4-methyl-1-piperazinyl)-1,2-dihydro-pyrrolo[3,2,1-ij]quinoline-5-carboxylic acid
8. Reference compound: 8-(4-methyl-1-piperazinyl)-9-fluoro-5-methyl-6,7-dihydro-1-oxo-1H,5H-benzo[ij]-quinolidine-2-carboxylic acid

[Test microorganisms]

A: *Staphylococcus aureus* FDA 209P
B: *Streptococcus pyogenes* II D S-23
C: *Escherichia coli* NIHJ JC-2
D: *Escherichia coli* No. 29
E: *Klebsiella pneumoniae* NCTC 9632
F: *Proteus mirabilis* 1287
G: *Proteus morganii* II D Kono
H: *Serratia marcescens* IFO 12648
I: *Acinetobacter calcoaceticus* AC-54
J: *Pseudomonas aeruginosa* ATCC 10145
K: *Pseudomonas aeruginosa* E-2

TABLE 1

| Test micro-organisms | Compound 1 | | Compound 2 | | Compound 3 | |
|---|---|---|---|---|---|---|
| | $1 \times 10^8$ | $1 \times 10^6$ | $1 \times 10^8$ | $1 \times 10^6$ | $1 \times 10^8$ | $1 \times 10^6$ |
| A | 0.39 | 0.2 | 0.78 | 0.39 | 0.39 | 0.2 |
| B | 3.13 | 3.13 | 6.25 | 3.13 | 12.5 | 12.5 |
| C | 0.1 | 0.05 | 0.1 | 0.1 | 0.2 | 0.2 |
| D | 0.1 | 0.1 | 0.1 | 0.1 | 0.39 | 0.2 |
| E | 0.2 | 0.2 | 0.2 | 0.1 | 0.39 | 0.39 |
| F | 0.78 | 0.39 | 0.2 | 0.2 | 1.56 | 0.78 |
| G | 0.39 | 0.2 | 0.39 | 0.2 | 0.39 | 0.39 |
| H | 0.2 | 0.2 | 0.2 | 0.2 | 0.78 | 0.78 |
| I | 0.39 | 0.39 | 3.13 | 0.78 | 1.56 | 0.78 |
| J | 1.56 | 0.78 | 0.39 | 0.39 | 6.25 | 3.13 |
| K | 1.56 | 0.78 | 0.39 | 0.39 | 6.25 | 6.25 |

| Test micro-organisms | Compound 4 | | Compound 5 | | Compound 6 | |
|---|---|---|---|---|---|---|
| | $1 \times 10^8$ | $1 \times 10^6$ | $1 \times 10^8$ | $1 \times 10^6$ | $1 \times 10^8$ | $1 \times 10^6$ |
| A | 0.39 | 0.39 | 0.39 | 0.2 | 0.78 | 0.39 |
| B | 25 | 25 | 12.5 | 6.25 | 12.5 | 6.25 |
| C | 0.78 | 0.78 | 0.78 | 0.39 | 1.56 | 0.78 |
| D | 1.56 | 1.56 | 0.78 | 0.78 | 1.56 | 1.56 |
| E | 3.13 | 1.56 | 0.78 | 0.78 | 6.25 | 1.56 |
| F | 6.25 | 6.25 | 1.56 | 1.56 | 6.25 | 6.25 |
| G | 1.56 | 1.56 | 1.56 | 1.56 | 6.25 | 6.25 |
| H | 6.25 | 6.25 | 3.13 | 1.56 | 6.25 | 6.25 |
| I | 6.25 | 6.25 | 6.25 | 3.13 | 6.25 | 6.25 |
| J | 25 | 12.5 | 6.25 | 6.25 | 12.5 | 6.25 |
| K | 25 | 25 | 12.5 | 6.25 | 12.5 | 1.56 |

TEST 2

(Measurement of concentration of compounds in blood and in urine)

The same Test Compound 1 as used in the above Test 1 was orally administered in a dose of 25 mg/kg to three male rats (weighing 190–242 g), and blood and urine were collected from the animals at intervals. The concentration of the test compound in the collected urine and blood was measured by a thin layer plate cup (6 ml medium/$\phi$90 mm shall) method wherein *Bacillus subtilis* ATCC 6633 was used as a test microorganism and a sensitive medium (manufactured by Eiken Kagaku K.K., Japan) was used as a medium. The results are shown in Table 2 (the concentration in urine) and in Table 3 (the concentration in blood), respectively.

TABLE 2

| Test Comp. No. | Time after administration | Recovered amount (μg) | Recovery rate (%) |
|---|---|---|---|
| Compound 1 | 0–24 hours | 1471.6 | 27.2 |

TABLE 3

| Test Comp. No. | Concentration in blood (μg/ml) Time after the administration (hour) | | | | | |
|---|---|---|---|---|---|---|
| | 0.5 | 1 | 2 | 4 | 6 | 8 |
| Compound 1 | 3.19 | 2.49 | 1.92 | 0.90 | 0.60 | 0.31 |

TEST 3

(Therapeutic effects of compounds in urinary infectious diseases in vivo)

*Pseudomonas aeruginosa* E-2 was cultured in a nutrient medium at 37° C. for 18 hours and the culture broth thus obtained was diluted with the same medium to prepare a solution of the microorganism (cell concentration: $10^7$ cells/ml). To the solution were dipped a UV-sterilized disc [glyceryl monomyristate (manufactured by Nikko Chemicals, Japan) and sodium cetylsulfurate (manufactured by Nikko Chemicals, Japan) in a weight ratio of 9:1; diameter: 2.0 mm, length: 3.0 mm] under ice-cooling for 1.5 hour to give a microorganism-containing disc for inoculation.

The above-prepared disc was surgically inserted into the bladder of JCL:S.D. female rats (one group: four rats) anaesthetized with secobarbital sodium. After the animals have been infected with the microorganism, i.e. 6 hours after the insertion of the disc, 1% oxamide-containing feed and water were administered to the animals. The oxamide-containing feed was changed to a normal feed after 24 hours. Test compounds 1, 7 and 8 as used in Test 1 (in the form of a 0.5% CMC suspension) were each orally administered to the animals in a dose of 16 mg/kg, 8.0 mg/kg, 4.0 mg/kg, 2.0 mg/kg, and 1.0 mg/kg at 6, 24 and 48 hours after the insertion of disc. After 4 days from the infection, urine was collected and further the kidney was taken out from the animals, and then the presence of microorganism was checked as to the collected urine and kidney. That is, 0.1 ml of the urine was applied onto an agar plate medium and cultured at 37° C. for 18 hours, and the number of colonies was counted. Besides, the taken out kidney was divided into two, and the plain section was contacted to an agar plate medium, and the medium was cultured likewise, and the number of colonies was counted, likewise. When the number of colonies was less than 10, it was evaluated as "effective," and when the number of colonies was more than 10, it was evaluated as "ineffective". In each group of mice, there were counted the number of mice where it was evaluated as "effective", and based on the data, there was calculated the 50% effective dose (ED$_{50}$) of the test compounds by Probit method. The results are shown in Table 4.

TABLE 4

| Test compound No. | ED$_{50}$ (mg/kg) |
|---|---|
| Test compound 1 | 1.53 |

TABLE 4-continued

| Test compound No. | $ED_{50}$ (mg/kg) |
| --- | --- |
| Test compound 7 | 6.15 |
| Test compound 8 | 12.0 |

| Preparation 1 | |
| --- | --- |
| Ingredients | Amount |
| Compound of Example 3 (HCl salt) | 200 mg |
| Glucose | 250 mg |
| Distilled water for injection | q.s. |
| totally | 5 ml |

The compound of Example 3 (HCl salt) and glucose are dissolved in distilled water for injection, and the mixture is poured into a 5 ml ampoule. The ampoule is purged with nitrogen gas and sterilized at 121° C. under pressure for 15 minutes to give an injection preparation.

| Preparation 2 | |
| --- | --- |
| Ingredients | Amount |
| Compound of Example 4 | 100 g |
| Avicel (a trademark of microcrystalline cellulose, manufactured by Asahi Chemicals) | 40 g |
| Cornstarch | 30 g |
| Magnesium stearate | 2 g |
| TC-5 (a trademark of hydroxypropyl cellulose, manufactured by Shinetsu Kagaku K.K.) | 10 g |
| Polyethylene glycol 6000 | 3 g |
| Castor oil | 40 g |
| Methanol | 40 g |

The compound of Example 4, avicel, cornstarch and magnesium stearate are mixed and ground, and the mixture is tabletted with a tabletting machine R 10 mm. The tablets thus obtained are coated with a film coating agent consisting of TC-5, polyethylene glycol 6000, castor oil and methanol to give film-coated tablets.

| Preparation 3 | |
| --- | --- |
| Ingredients | Amount |
| Compound of Example 5 | 2 g |
| Purified lanoline | 5 g |
| Bleached bees wax | 5 g |
| White vaseline | 88 g |
| Totally | 100 g |

Bleached bees wax was warmed until it becomes liquid, and thereto are added the compound of Example 5, purified lanoline and white vaseline. The mixture is heated until it becomes liquid, and thereafter stirred until it starts to solidify to give an ointment.

| Preparation 4 | |
| --- | --- |
| Ingredients | Amount |
| Compound of Example 11 (HCl salt) | 200 mg |
| Glucose | 250 mg |
| Distilled water for injection | q.s. |
| Totally | 5 ml |

The compound of Example 11 (HCl salt) and glucose are dissolved in distilled water for injection, and the solution is poured into a 5 ml ampoule. The ampoule is purged with nitrogen gas and then sterilized by heating at 121° C. under pressure for 15 minutes to give an injection preparation.

What is claimed is:

1. A benzo-heterocyclic compound of the formula:

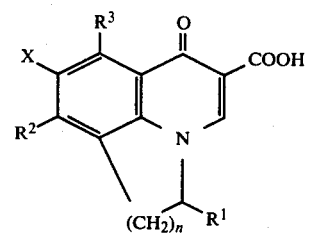

wherein
   $R^1$ is a lower alkyl group;
   $R^2$ is a piperazinyl group or a substituted piperazinyl group wherein the substituent is a lower alkyl group or a hydroxy group;
   $R^3$ is an amino group;
   X is a halogen atom; and
   n is an integer of 1,
and a pharmaceutically acceptable salt thereof.

2. The compound of claim 1, wherein
   $R^1$ is methyl or ethyl; and
   X is a chlorine or fluorine atom.

3. The compound according to claim 1, wherein $R^1$ is methyl group, $R^2$ is a 4-lower alkyl substituted 1-piperazinyl group, and X is fluorine.

4. The compound according to claim 1, which is 8-fluoro-2-methyl-9-(4-methyl-1-piperazinyl)-7-amino-6-oxo-1,2-dihydro-pyrrolo[3,2,1-ij]quinoline-5-carboxylic acid.

5. An antimicrobial composition comprising an antimicrobially effective amount of a benzo-heterocyclic compound of the formula:

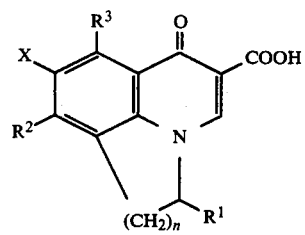

wherein
   $R^1$ is a lower alkyl group;
   $R^2$ is a piperazinyl group or a substituted piperazinyl group wherein the substituent is a lower alkyl group or a hydroxy group;
   $R^3$ is an amino group;
   X is a halogen atom; and
   n is an integer of 1;
and a pharmaceutically acceptable salt thereof in admixture with a pharmaceutically acceptable carrier or diluent.

* * * * *